United States Patent [19]

Bellis

[11] 4,130,595

[45] Dec. 19, 1978

[54] MELT OXYCHLORINATION PROCESS

[75] Inventor: Harold E. Bellis, Hockessin, Del.

[73] Assignee: E. I. Du Pont de Nemours and Company, Wilmington, Del.

[21] Appl. No.: 716,292

[22] Filed: Aug. 20, 1976

Related U.S. Application Data

[63] Continuation of Ser. No. 547,017, Feb. 4, 1975, abandoned, which is a continuation-in-part of Ser. No. 206,157, Dec. 8, 1971, abandoned, and Ser. No. 764,649, Oct. 2, 1968, and Ser. No. 740,762, Jun. 27, 1968, Pat. No. 3,583,949.

[51] Int. Cl.$^2$ .............................................. C07C 21/00
[52] U.S. Cl. ............................. 260/654 R; 260/654 D
[58] Field of Search .......... 260/654 A, 654 R, 654 D, 260/658 R, 659 A

[56] References Cited

U.S. PATENT DOCUMENTS

| | | | |
|---|---|---|---|
| 2,140,508 | 12/1938 | Reilly | 260/658 R |
| 2,447,323 | 8/1948 | Fontana | 260/659 A |
| 3,222,408 | 12/1965 | Smith | 260/659 R |
| 3,363,010 | 1/1968 | Schwarzenbek | 260/648 |
| 3,557,229 | 1/1971 | Riegel | 260/659 A |
| 3,671,596 | 6/1972 | Bellis | 260/654 R |
| 3,697,608 | 10/1972 | Bellis | 260/654 D |

FOREIGN PATENT DOCUMENTS

| | | | |
|---|---|---|---|
| 1907764 | 9/1969 | Fed. Rep. of Germany | 260/654 A |
| 1213402 | 11/1970 | United Kingdom | 260/654 A |

*Primary Examiner*—Delbert E. Gantz
*Assistant Examiner*—Joseph A. Boska

[57] ABSTRACT

A melt oxychlorination process which produces trichloroethylene and perchloroethylene by chlorinating $C_2$ hydrocarbons and their incompletely chlorinated derivatives containing at least 50% by weight of 1,1,2-trichloroethane, dichloroethylene, or both together, with a melt consisting essentially of iron chloride, copper chloride and alkali metal chloride by dispersing the material to be chlorinated in the melt whereby said material is chlorinated by the melt, wherein certain alkali metal chlorides, proportions thereof, and process conditions are utilized to provide desired product selectivity.

5 Claims, No Drawings

MELT OXYCHLORINATION PROCESS

CROSS-REFERENCE TO RELATED APPLICATIONS

This application is a continuation of copending application Ser. No. 547,017, filed Feb. 4, 1975, now abandoned, which is a continuation-in-part of applications Ser. No. 740,762, filed June 27, 1968 now U.S. Pat. No. 3,583,949; Ser. No. 764,649, filed Oct. 2, 1968, pending; and Ser. No. 206,157, filed Dec. 8, 1971, now abandoned.

BACKGROUND OF THE INVENTION

Many methods have been proposed in the prior art for randomly or selectively producing chlorinated hydrocarbons from hydrocarbons and/or chlorohydrocarbons in processes involving modified Deacon-type chlorination procedures. In processes of this character, oxygen, the hydrocarbon and/or chlorohydrocarbon to be chlorinated, and chlorine or HCl as the chlorinating agent, are brought into contact at elevated temperatures with a metal halide catalyst, usually a copper chloride-containing catalyst. Where HCl is utilized as the feed material, it is believed that a preliminary oxidation of the HCl takes place resulting in the formation of water and elemental chlorine. The chlorine produced then reacts with the hydrocarbon and/or chlorohydrocarbon feed to produce further quantities of HCl and a chlorinated derivative of the feed material. When chlorine is utilized as the chlorinating agent, it is believed that an initial chlorination of the hydrocarbon and/or chlorohydrocarbon takes place which generates HCl. The HCl thus generated is converted by the conventional Deacon reaction to chlorine and water.

In recent years considerable emphasis has been laid on fluid bed processes for conducting such oxychlorination procedures since the reactions involved are highly exothermic and the removal of heat usually becomes a problem of considerable moment. In conducting fluidized bed oxychlorination procedures of this type, however, many difficulties are encountered. For example, in some instances the fluidized bed does not provide sufficient contact with the initial feed to produce complete chlorination or high yields of substitutive chlorination. Also, the fluidized bed becomes hard to handle in high temperature chlorination procedures. Consequently, many methods have been devised for providing adequate cooling of the fluidized bed catalyst particles employed during reaction. Various carriers have been tested to determine the best materials from the standpoint of thermal conductivity, lack of attrition during fluidization, and other similar considerations in order to arrive at a material suitable for use as a support for the catalyst material employed during the chlorination reaction. Product recovery from the reaction zones without injuring the catalyst particles is also another problem encountered in this area. Many of the gas mixtures fed are highly explosive under certain conditions so that proper mixing of them is an extremely important factor. In addition, corrosion of materials of construction utilized in forming the reactors involved, and the selection of the proper size of the reactors for the purpose of providing maximum productivity are also problems. It has also been found that when conducting these processes in large reactors (two feet or more in diameter), a considerable sacrifice in overall efficiency of the process contemplated is experienced.

The commercial success of these processes is due largely to the demand for halogenated compounds containing from 1 to 10 carbon atoms; however, there is a great need for improvement of these processes. For example, it would be highly desirable to reduce the contact time normally associated with fixed bed operations, while eliminating the difficulties associated with fluidized solids operation such as catalyst attrition and catalyst vaporization which appears to be more pronounced with highly active catalysts. While the moving bed solves some of these difficulties, it is not without its own particular problems such as those derived from the mechanical transportation of catalysts throughout a zone and the existence of "hot spots" in the catalyst bed. The heat of reaction generated on the surface of the solid permits direct oxidation of the hydrocarbon and/or chlorohydrocarbon to produce undesirable oxides of carbon.

The more active metal halide catalysts such as, copper chloride, are more volatile at required halogenation temperatures and thus, it is difficult to retain the catalyst in the system and maintain the activity of the catalyst mass over an extended period of time. In such systems the volatilized catalyst must be recovered by condensation or other troublesome methods and returned in a supported state to the reaction zone. Thus, the economics of operating with fluidized catalysts is poor in spite of the fact that such a system provides better temperature control and higher yield of product for a given period of operation.

Therefore, it is readily apparent that a new chlorination process is needed with overcomes the above difficulties by providing a more economic and commercially feasible chlorination process. Additionally, a better chlorination process is desired to provide improved contact between the hydrocarbon and/or chlorohydrocarbon and chlorinating agents in conjunction with good temperature control of the reaction zone. Furthermore, a selective chlorination process (i.e., a process that produces predominantly one specific chlorinated product in high yields) is in great demand throughout the industry.

SUMMARY OF THE INVENTION

This invention relates to an oxychlorination process which comprises chlorinating a material of the group consisting of $C_2$ hydrocarbons, incompletely chlorinated derivatives of $C_2$ hydrocarbons, and mixtures thereof, containing at least 50% by weight 1,1,2-trichloroethane at a temperature within the range of 300° C.–500° C., by means of a melt consisting essentially of iron chloride, copper chloride and alkali metal chloride(s) by dispersing the material to be chlorinated in the melt whereby said material is chlorinated by the melt, wherein:

(a) the alkali metal chloride is selected from the group consisting of sodium chloride, potassium chloride, rubidium chloride, cesium chloride, and mixtures thereof;

(b) the mole ratio of iron chloride to copper chloride is from about 0.1:1 to about 2:1;

(c) the mole ratio of alkali metal chloride to the combined moles of iron and copper chlorides is from about 0.5:1 to about 2:1; and (d) at least some of the copper chloride is maintained as cupric chloride and substantially all of the iron chloride is maintained as ferric chloride.

DESCRIPTION OF THE PREFERRED EMBODIMENTS

The preferred process of this invention involves chlorinating 1,1,2-trichloroethane, otherwise known as β-trichloroethane, to produce high yields of trichloroethylene and perchloroethylene by contacting the 1,1,2-trichloroethane with the above-described melt. In addition, the process of this invention is equally applicable to the chlorination of mixtures of 1,1,2-trichloroethane or dichloroethylene, many other $C_2$ hydrocarbons and their incompletely chlorinated derivatives, and more specifically, to $C_2$ unsaturated hydrocarbons and their chlorinated derivatives, provided such mixtures contain at least 50% by weight 1,1,2-trichloroethane, dichloroethylene, or both together. However, since 1,1,2-trichloroethane is one of the preferred starting materials, much of the discussion throughout the specification is directed to the chlorination of 1,1,2-trichloroethane.

It is pointed out that when chlorinating 1,1,2-trichloroethane, the preferred process of this invention effects a high selectivity toward trichloroethylene and perchloroethylene. The terminology "high selectivity" is intended to designate that at least 50 mole percent of the chlorinated product comprises trichloroethylene and perchloroethylene with a preferred selectivity being at least 70% trichloroethylene and perchloroethylene. Also, a high ratio of trichloroethylene to perchloroethylene is desired since trichloroethylene is presently of greater commercial importance.

The preferred process of this invention is also directed to producing "high yields" of chlorinated hydrocarbons. In this invention, the terminology "high yields" means that a high percentage (at least 90%) of the starting material is converted to chlorinated hydrocarbons, with the yield losses being represented by CO, $CO_2$ and any other oxygen-containing byproducts. In order to achieve high yields, the melt composition (e.g., $FeCl_3$, $CuCl_2$, KCl, etc.), temperature, HCl partial pressure and oxide content must be optimized within the teachings of this invention.

Accordingly, the preferred embodiment is directed to a chlorination process which comprises chlorinating a starting material consisting essentially of 1,1,2-trichloroethane at a temperature within the range of 350° C.–450° C. by means of a melt comprising iron chloride, copper chloride and alkali metal chloride(s) by dispersing the starting material in the melt whereby said material is chlorinated by the melt, wherein:

(a) the alkali metal chloride is selected from the group consisting of potassium chloride and a mixture of sodium chloride and potassium chloride;

(b) the mole ratio of iron chloride to copper chloride is from about 0.2:1 to about 1:1;

(c) the mole ratio of alkali metal chloride to total iron and copper chlorides is from about 0.7:1 to about 1.3:1; and (d) all of the iron chloride is maintained as ferric chloride and some of the copper chloride is maintained as cupric chloride.

Generally as ethylene is chlorinated, with the progressive addition of chlorine and splitting out of HCl, the chlorination products are as follows: ethylene dichloride (1,2-dichloroethane-$C_2H_4Cl_2$), vinyl chloride ($C_2H_3Cl$), 1,1,2-trichloroethane ("β-TRI"-$C_2H_3Cl_3$), dichloroethylene ("DCE"-$C_2H_2Cl_2$), tetrachloroethane ($C_2H_2Cl_4$), trichloroethylene ("TRI"-$C_2HCl_3$), pentachloroethane ($C_2HCl_5$), perchloroethylene ("PER"-$C_2Cl_4$) and hexachloroethane ($C_2Cl_6$). The employment of the various process parameters of this invention results in a high selectivity of product which contains at least 50% trichloroethylene and perchloroethylene in the preferred embodiment, with smaller amounts of the incompletely chlorinated derivatives (e.g., tetrachloroethane) being produced; very minor amounts of the more completely chlorinated derivatives (e.g., pentachloroethane and hexachloroethane) may also be produced.

The chlorination process of this invention involves the use of a particular melt which contains certain metal chlorides in critical proportionate amounts to produce the desired selectivity of product. The essential components of the melt composition are ferric chloride, cupric chloride and alkali metal chloride(s). The ferric chloride and cupric chloride are considered to have at least two functions; they act as chlorinating agents and also as dehydrohalogenating agents. The function of the alkali metal chloride(s) is to reduce the vapor pressure of ferric chloride and also to modify the chlorinating power of the ferric chloride and cupric chloride in order that the chlorination reaction can be stopped selectively. The alkali metal chloride also is necessary to produce a melt and to moderate the dehydrohalogenating (HCl cracking) reaction.

Since ferric chloride and cupric chloride are the chlorinating agents, there must be some of each chloride present in the melt at all times. Therefore, one of the essential features of this invention is that at least some of the iron chloride and copper chloride be maintained as ferric chloride and cupric chloride. The numerical amount is not significant in the broad scope of the invention; any small amounts of ferric chloride and cupric chloride provide an operable process. In the preferred process of the invention, the critical requirement concerning this aspect is that some of the copper chloride be maintained as cupric chloride. As a practical matter, whenever some cupric chloride is present, substantially all of the iron chloride will be ferric chloride since some cupric chloride oxidizes any ferrous chloride to ferric chloride. It is pointed out that with a mixture of cupric chloride and ferrous chloride, the cupric chloride will automatically oxidize the ferrous chloride to ferric chloride since cupric chloride is a stronger oxidizing agent than ferric chloride in salt baths of the type used in this invention.

The proportions of iron chloride and copper chloride are a critical feature of the invention. Generally, the mole ratio of iron chloride to copper chloride is from about 0.1:1 to about 2:1. The preferred ratio ranges from about 0.2:1 to about 1:1. While the use of larger or smaller amounts of these chlorides will chlorinate and provide an operable process, the selective process of this invention will not tolerate any variation in proportions outside of the above-specified ranges.

If the bath contained iron chloride but no copper chloride, the resulting chlorinated hydrocarbon would be principally dichloroethylene, a cracking rather than chlorinating reaction. If the bath contained copper chloride but no iron chloride, the reaction cannot readily be controlled, except at low oxidation levels where the productivity is low, and tends to produce only perchloroethylene which is economically less desirable than trichloroethylene.

Preferably, the invention is operated with the bath at an oxidation level less than 70%, and even more preferably less than 50%. The oxidation level is defined as the mole percentage of total copper and iron chlorides that is present in the cupric and ferric states. With both cupric and ferric chlorides present, it appears that the cupric salt preferentially chlorinates 1,1,2-trichloroethane to perchloroethylene at higher oxidation levels. Increasing amounts of chlorination in such baths of 1,1,2-trichloroethane to trichloroethylene is effected by ferric chloride at lower oxidation levels. Also, the higher the oxidation level, generally the greater the efficiency of chlorination. By operating at an oxidation state which maintains only a small proportion of the copper chloride as cupric chloride, production of trichloroethylene is maximized with a minimum loss of efficiency.

The alkali metal chlorides that are suitable include KCl, NaCl, RbCl and CsCl. The presence of these chlorides is necessary to produce a liquid phase with the ferric chloride and cupric chloride, to depress the volatility of the ferric chloride at operating temperatures and to obtain a melt which will have selective chlorinating power. The mole ratio of alkali metal chloride to the combined amount (moles) of iron chloride and copper chloride should be from about 0.5:1 to about 2:1. These are critical proportions. Below 0.5 mole alkali chloride per total moles iron chloride and copper chloride, there is not enough alkali metal chloride to tie up the iron and copper chlorides and prevent these chlorides from volatilizing out of the reactor. If the amount of alkali metal chloride is over 2 moles per combined mole of iron and copper chlorides, the vapor pressure of the chlorine is diminished and an insufficient amount of chlorination results. Also, at these high alkali metal chloride ratios, the melting point of the metal chloride mixture is too high so that the melt system becomes too difficult to operate. The preferred ratio is from 0.7:1 to 1.3:1.

The broadest aspects of the invention include the use of KCl, NaCl and mixtures thereof. The rate and degree of chlorination varies with each chloride. When chlorinating 1,1,2-trichloroethane to trichloroethylene and perchloroethylene, sodium chloride tends to produce mainly perchloroethylene. Therefore, either potassium chloride alone or a mixture of sodium chloride and potassium chloride should be utilized when trichloroethylene is the preferred product.

Also, potassium chloride is preferred for its ability to keep the water content of the bath low to obtain high yields and good chlorinating ability. Lithium chloride is not used because of the degree to which it would hold water in the melt.

The temperature at which the melt chlorination process of this invention is carried out is generally within the range of 300° C.–500° C. The temperature range is dependent upon the metal chloride salt mixture which is utilized, the proportions of each salt and the desired product. A temperature within the range of 350° C.–450° C. is preferred when chlorinating 1,1,2-trichloroethane to trichloroethylene and perchloroethylene. If the temperature is decreased such as below 300° C., the product mix will contain smaller amounts of trichloroethylene and perchloroethylene. On the other hand, as the temperature is increased, such as above 450° C., the product mix will contain greater amounts of hexachloroethane.

It is desirable that the oxides of copper and iron ($Fe_2O_3$ and CuO) be absent from the melt. Experience has shown, however, that up to 5 weight percent of these oxides may be tolerated with the preferred range being 0–0.5 weight percent of the melt. The presence of these oxides contributes to low yields. Chlorine-containing gases introduced in the regeneration process convert such oxides and any oxychlorides back to the chlorides.

The pressure employed in the chlorination process can vary considerably and be as high as 50 atmospheres. A pressure within the range of 1 to 10 atmospheres is preferred. The pressure utilized is restricted by materials of construction and the problems of handling the melt at the high operating temperatures of this invention.

The atmosphere employed in the melt and surrounding the melt is not extremely critical. However, in the preferred chlorination process, it is essentially free of any substantial amount of added elemental chlorine. This terminology is intended to exclude the presence or addition of free chlorine to the reaction zone for the purpose of directly chlorinating the hydrocarbon. Since this process involves using the melt itself as the chlorinator, no free elemental chlorine is required or used to directly chlorinate the hydrocarbon. However, the melt itself might give off minor amounts of elemental chlorine through decomposition of the metal chlorides. Also, free chlorine may be added to the reaction zone to regenerate the melt. However, the chlorine, even when premixed with the feed, will preferentially oxidize (chlorinate) the CuCl to $CuCl_2$ rather than enter into the hydrocarbon chlorination reaction. Therefore, the terminology "atmosphere essentially free of elemental chlorine" is intended to permit the presence, in the reaction zone, of minor amounts of elemental chlorine which are given off by the melt, or used to regenerate, but not the presence or addition of any elemental chlorine, separate and apart from the melt, which would in fact chlorinate the hydrocarbon.

The starting materials suitable for the chlorination reactions described herein include any saturation and unsaturated hydrocarbons, including their chlorinated derivatives. However, the selective process of this invention is mainly concerned with chlorinating $C_2$ hydrocarbons and their incompletely chlorinated derivatives. For example, ethylene, vinyl chloride, dichloroethylenes, ethyl dichloride, ethylene dichloride, along with the required 1,1,2-trichloroethane, dichloroethylene, or mixtures thereof, are the preferred starting materials.

The process of this invention involves providing good contact between the hydrocarbon gas and the melt. An effective method that may be used is to disperse the gas in the body of the melt. The dispersal may be effected by forcing the gas, in the form of fine bubbles, to ascend through the melt, by any known means. Typical means include porous plates, or porous trimbles, a suitable bubbling apparatus or a sparger. A stirring apparatus may also be used. Several stages may be used, with the gas being dispersed into the melt at several different positions in the apparatus, while the melt is passed continuously from one stage to another. An essential requirement is that the hydrocarbon gas be dispersed and finely distributed throughout the melt to provide good contact between the hydrocarbon gas and the melt, and to obtain a reasonable reaction rate. The size or fineness of the bubbles also has an effect on the reaction rate. The reaction rate increases directly with an increase in the fineness of the hydrocarbon gas bubbles, an increase in the amount of agitation utilized to disperse the hydrocarbon gas in the melt, or any increased overall contact of the hydrocarbon gas with the melt. However, the scope of this invention is not intended to be limited to any particular dispersing mechanisms. Comparatively speaking, if slower reaction rates and chlorination rates can be tolerated, there is no necessity for a thorough dispersion of the hydrocarbon gas in the liquid melt as is required in the preferred embodiment of the invention.

The process of this invention can be carried out as follows: the required amounts of each metal salt, in solid form, are mixed together to obtain even distribution of the respective salts in the salt mixture. This salt mixture is added to a reaction vessel where it is heated to a temperature within the range of 300° C.–500° C. whereby a melt of the salt mixture is obtained. If any of the metal salts were melted separately, it would vaporize and boil off (e.g., sublime at high temperatures). If the alkali metal salts were melted separately, very high temperatures would be required since they have high melting points. Therefore, by using a mixture of the metal salts, a melt or molten solution of the metal salts can be readily obtained at the operating temperatures of this process.

Then 1,1,2-trichloroethane ($\beta$-Tri), or any other suitable hydrocarbon or chlorohydrocarbon, is fed to the reaction vessel through any appropriate inlet means. It is a matter of choice and designing skill to decide whether the ethylene enters through the side, top or bottom of the reaction vessel. It is preferred, however, that the $\beta$-Tri enter the reaction vessel near the bottom to give the $\beta$-Tri a longer contact time with the melt. The $\beta$-Tri is chlorinated and the chlorinated hydrocarbon reaction products, containing at least 50% trichloroethylene and perchloroethylene, begin to vaporize and rise to the top of the reaction vessel. An outlet is provided, usually at the top of the reaction vessel, where the reaction products can be drawn off; a condensation system, and possibly a scrubber system, could also be provided to recover and/or recycle any unreacted ethylene.

The above-described process is essentially a batch-type process; when the oxidation level of the melt reaches a point where there is insufficient ferric chloride and cupric chloride, this batch process would not chlorinate to the desired high selectivity and high yield of trichloroethylene and perchloroethylene. The batch process would have to be stopped in order to regenerate the melt. A suitable batch operation can be carried out by alternatively chlorinating the starting materials, and then regenerating the melt with a chlorine-containing gas, a combination of an oxygen-containing gas and hydrogen chloride, or a mixture thereof prior to the next chlorination run.

A preferred regenerating system comprises a combination of an oxygen-containing gas and hydrogen chloride. This includes the use of mixtures of an oxygen-containing gas and HCl as well as the stepwise use of an oxygen-containing gas and HCl (and vice versa). Any regenerating procedures involving the use of an oxygen-containing gas and hydrogen chloride are applicable.

The terminology "a chlorine-containing gas" includes free elemental chlorine, a mixture of chlorine and oxygen, a mixture of chlorine and hydrogen chloride, and mixtures of chlorine and any other gases which are compatible with the chlorination system, as well as solid or liquid compounds that generate chlorine in the hot salt bath. The terminology "an oxygen-containing gas" encompasses free elemental oxygen and mixtures of oxygen and other gases which are compatible with the chlorination system. Air is an economical oxygen-containing gas which can be used.

The preferred process of this invention is a continuous process whereby the melt is continually chlorinating 1,1,2-trichloroethane, being regenerated, and/or recycled. The continuous process of this invention can be operated as either a single-stage operation or a multistage operation. In a single-stage continuous process, one reaction vessel is used. While the chlorination is taking place and the ferric chloride and cupric chloride are being reduced to ferrous chloride and cuprous chloride, a chlorine-containing gas, a mixture of an oxygen-containing gas and hydrogen chloride, or a mixture thereof is added to regenerate the melt. Thus, the 1,1,2-trichloroethane is continuously chlorinated by the melt and drawn off in high yields of trichloroethylene and perchloroethylene at the same time that the melt is being regenerated to provide the required ferric chloride and cupric chloride to chlorinate. If a chlorine-containing gas is added to regenerate the melt, the chlorine may be supplied in a separate section or zone of the reaction vessel so that the atmosphere in the reaction zone is essentially free of any substantial amount of elemental chlorine but this is not essential. A suitable reaction vessel might contain a central conical section for reacting the hydrocarbon with the melt and a separate side section between the conical section and the walls of the vessel for regeneration of the reduced melt. However, the preferred and advantageous vessel would not contain any separated sections. Therefore, any vessel not having separate sections is operable, as demonstrated by the examples.

The multi-stage continuous process requires use of two or more vessels or reaction zones. The first vessel would be the reaction vessel in which the actual chlorinating is done. The reduced melt containing cuprous chloride and ferrous chloride would then be pumped to another vessel to be oxidized and thereby regenerated to the ferric and cupric states. Into the second and any succeeding vessels is introduced a combination of an oxygen-containing gas (e.g., air) and HCl, a chlorine-containing gas or a mixture thereof. However, if sufficient oxygen is supplied with the hydrocarbon feed stream to maintain the oxidation level of the bath, hydrogen chloride alone can be supplied in the regeneration procedure to eliminate water from the reaction zone and to minimize oxide content. Also, any by-product water may be removed from the melt in the regeneration zone or in a separate zone such as by evaporation or preferably by flushing with hydrogen chloride, nitrogen or other suitable gases. The regenerated melt containing ferric chloride and cupric chloride would then be recycled to the original reaction vessel to chlorinate the $\beta$-TRI.

The amount of oxygen absorbed by the melt is controlled by the rate of passage of the oxygen-containing gas over and through the melt in the regeneration contact zone(s), the pressure of the oxygen-containing gas, the length of the contact zone and the efficiency of the overall regeneration system. Moderate pressures generally give rapid and efficient absorption of oxygen in the melt although operations at atmospheric pressure give satisfactory results. Air pressures between 1 and 50 atmospheres may be employed, however, the preferred range is between 1 and 10 atmospheres. When air is utilized as the gas, absorption of from 35 to 75 percent of the oxygen from the contacting air is readily obtainable. In general, if oxygen is used in the reactant feed stream, all the oxygen from the air passing through the regeneration zone should be absorbed in the bath to avoid explosive mixtures in the product stream.

The principal chlorination and regeneration reactions of the invention are as follows:

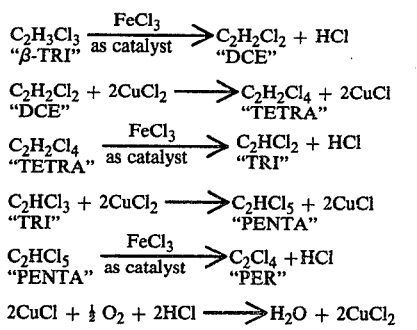

$$(1) \quad C_2H_3Cl_3 \xrightarrow{FeCl_3 \text{ as catalyst}} C_2H_2Cl_2 + HCl$$
$$\text{"}\beta\text{-TRI"} \qquad\qquad\qquad \text{"DCE"}$$

$$(2) \quad C_2H_2Cl_2 + 2CuCl_2 \longrightarrow C_2H_2Cl_4 + 2CuCl$$
$$\text{"DCE"} \qquad\qquad\qquad \text{"TETRA"}$$

$$(3) \quad C_2H_2Cl_4 \xrightarrow{FeCl_3 \text{ as catalyst}} C_2HCl_3 + HCl$$
$$\text{"TETRA"} \qquad\qquad\qquad \text{"TRI"}$$

$$(4) \quad C_2HCl_3 + 2CuCl_2 \longrightarrow C_2HCl_5 + 2CuCl$$
$$\text{"TRI"} \qquad\qquad\qquad \text{"PENTA"}$$

$$(5) \quad C_2HCl_5 \xrightarrow{FeCl_3 \text{ as catalyst}} C_2Cl_4 + HCl$$
$$\text{"PENTA"} \qquad\qquad\qquad \text{"PER"}$$

$$(6) \quad 2CuCl + \tfrac{1}{2}O_2 + 2HCl \longrightarrow H_2O + 2CuCl_2$$

An alternative regeneration reaction is as follows:

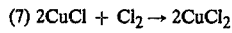

(7) $2CuCl + Cl_2 \rightarrow 2CuCl_2$

The melt chlorination system of this invention may also contain small amounts of water. Generally, the water content of the melt should not be greater than 3% based on the weight of the melt. The presence of larger amounts of water tends to produce high yield losses to CO and CO$_2$ and chloral.

Some of the most significant advantages can be summarized as follows:

(1) The process can be carried out in a single stage wherein all of the feed stock and regeneration gas can be simultaneously fed into one reactor. The melt does not have to be transported to different vessels but can remain in a single vessel.

(2) The process produces high yields of chlorinated products. In the preferred process there is less than 1% yield loss.

(3) The process is highly selective. At least 50% of the chlorinated products can be directed to trichloroethylene and perchloroethylene. These chlorinated products are made directly from the starting materials without any intermediate processing steps. Furthermore, the trichloroethylene and perchloroethylene products by this process are refineable by conventional distillation techniques due to the absence of or low content of methylchloroform, and unsymmetrical tetrachloroethane, which are difficult to separate.

(4) The HCl, which is present to regenerate, can be consumed in amounts ranging from 50-100%. This is considered to be a high HCl utilization rate in comparison with prior melt regeneration processes.

It is pointed out that the process of this invention is directed to chlorinating "by means of" a melt (molten salts) as distinguished from chlorinating "in" the melt or molten salt. It is the melt itself which does the chlorinating in the process of this invention and not any other liquid or gaseous additives. The process is significantly different from chlorinating with elemental chlorine because elemental chlorine gives a random product distribution whereas the process of this invention is selective and produces high yields. Chlorinating by means of a melt provides additional significant advantages over the prior chlorination processes. There is a uniform temperature throughout the melt and, consequently, a uniform chlorination rate. There is no agglomeration of catalyst particles as in a fluidized bed. More complete chlorination rates are available due to the presence of massive amounts of the chlorinating composition in the melt. In short, the melt chlorination process of this invention provides a more effective means for chlorinating.

The invention is illustrated by the following examples. In the examples and elsewhere in the specification, unless indicated otherwise, all parts, proportions and percentages of materials or components are in mole percent, based on the moles of melt.

EXAMPLE 1

Into a glass reactor containing 2.2 liters of a melt of 10 moles FeCl$_3$, 20 moles KCl, 8 moles CuCl and 2 moles CuCl$_2$ was passed $\beta$-Tri (1,1,2-trichloroethane) at the rate of 2 cc./minute. The oxidation level of this melt was 60%. The melt was mechanically stirred at a temperature of 425° C. under atmospheric pressure; oxygen was fed at the rate of 0.5 liters/minute. Approximately 79 mole percent of the $\beta$-Tri was converted to the product comprising 31% trichloroethylene, 34% perchloroethylene and 32% dichloroethylene. The ratio of Tri : Per was 0.9:1 and the oxygen conversion was 100%. There was no off gas nor were there any oxygenated chlorinated hydrocarbons detected in the product. The yield loss to CO and CO$_2$ was less than 0.1% and the oxidation level remained constant. Since no oxides were detected in the melt and there was little if any production of saturated compounds, regeneration was not necessary, but HCl can be used to flush the water out of the bath.

EXAMPLE 2

Into a glass reactor containing 2.2 liters of a melt comprising 10 moles FeCl$_3$, 8 moles CuCl, 2 moles CuCl$_2$ and 20 moles NaCl was passed 1,1,2-trichloroethane at the rate of 2 cc./minute. The oxidation level of the melt was 60%. The melt was mechanically stirred at a temperature of 425° C. under atmospheric pressure. Oxygen was also fed at the rate of 0.5 liters/minute. Approximately 93% of the $\beta$-Tri was converted to a product comprising 18% trichloroethylene, 42% perchloroethylene, 36% dichloroethylene. The oxygen conversion was 91% while a 20% yield loss to CO and CO$_2$ was observed. This demonstrates that NaCl used in place of KCl produces the desired products less efficiently as compared to Example 1. The melt could be regenerated with an adequate amount of HCl to return to the original oxidation level.

EXAMPLE 3

Other hydrocarbons were passed through the melt described in Example 1, and under the same operating conditions, illustrating that other hydrocarbons can be present in the feed stock along with 1,1,2-trichloroethane and dichloroethylene to produce trichloroethylene and perchloroethylene, although at reduced efficiencies.

Ethylene dichloride was chlorinated to a product comprising 30% trichloroethylene, 21% perchloroethylene, 21% dichloroethylene and 17% unconverted ethylene dichloride with a yield loss to CO and CO$_2$ of only 3%.

Vinyl chloride was chlorinated to a product comprising 21% trichloroethylene, 33% perchloroethylene, 15% β-trichloroethane and 12% unconverted vinyl chloride with a yield loss to CO and $CO_2$ of only 1%.

EXAMPLE 4

Dichloroethylene was chlorinated using the operating conditions of Example 1 to a product comprising 24% trichloroethylene, 22% perchloroethylene, and 52% unconverted dichloroethylene with a yield loss to CO and $CO_2$ of only 0.1%. There was no $Fe_2O_3$ in the melt. This demonstrates that a variety of starting materials can be chlorinated for the process of this invention.

EXAMPLE 5

Ethylene was passed at the rate of 1 liter/minute at various temperatures through a melt consisting of 8 moles CuCl, 2 moles $CuCl_2$, 10 moles $FeCl_3$, 20 moles KCl. The oxidation level of the melt was 60%. Oxygen and HCl were fed concurrently at the rate of 0.5 liter/minute. The yield loss to CO and $CO_2$ was measured at several temperatures from 350° C. to 450° C. The yield losses were about 25%, 15%, 5% 1%, 0% at 350° C., 375° C., 400° C., 425° C., 450° C., respectively, while conversion of ethylene to higher chlorinated hydrocarbons varied from 70 to 85%. No $Fe_2O_3$ was found in any instance. The water contents (weight %) of the melt were measured and found to be 3%, 2%, 1% at 350° C., 375° C., 425° C., respectively. This demonstrates the effect of temperature variation on yield loss. Although ethylene is used for this example instead of the β-Tri of the invention, ethylene is even more prone to oxidation than β-Tri, and therefor is useful for illustrating increased efficiency at higher temperatures.

EXAMPLE 6

Ethylene dichloride was passed at the rate of 2 cc./minute through a melt consisting initially of 8 moles CuCl, 2 moles $CuCl_2$, 8 moles $FeCl_3$, 1 mole $Fe_2O_3$ and 20 moles KCl at 425° C. The water content was about 1% by weight. The yield loss to CO and $CO_2$ was recorded as the oxide content was reduced to zero by reaction with byproduct HCl from the chlorination reaction. The yield losses to CO and $CO_2$ were about 10%, 2%, 1%, 0% when $Fe_2O_3$ levels were 2%, 1% and 0.5% by weight in the melt. The ethylene dichloride was converted to a product comprising 27% trichloroethane, 13% perchloroethylene, 30% dichloroethylene and 21% uncoverted ethylene dichloride. Although the feedstock for this example is outside the invention, the data illustrates benefits in yield derived from controlling the oxide content of the melt in similar systems.

EXAMPLE 7

β-Trichloroethane was passed at the rate of 2 cc./minute through a melt (425° C.) comprising 15 moles CuCl, 3 moles $CuCl_2$, 2 moles $FeCl_3$ and 20 moles KCl. The oxidation level of the melt was 25%. Oxygen was also introduced at the rate of 0.5 liters/minute. The oxygen was completely absorbed and there was no yield loss to CO or $CO_2$. Also, the HCl content of the aqueous phase in the product was only 6% indicating a 92% conversion of HCl to water. This is below the azeotrope composition of 15% HCl in water, permitting separation of HCl from the product to return to the reaction. The organic product comprised 23% trichloroethylene, 7% perchloroethylene, 20% trichloroethylene and 9% unreacted β-trichloroethane. No insoluble oxides were detected in the melt. This example shows the beneficial effect on HCl conversion by operating at high Cu/Fe ratios with a low oxidation level.

EXAMPLE 8

β-Trichloroethane was passed at the rate of 2 cc./minute through a melt (390° C.) consisting of 8 moles CuCl, 2 moles $CuCl_2$, 10 moles $FeCl_3$ and 20 moles KCl while stirring at various rates to produce different degrees of gas dispersion. The oxidation level of the melt was 60%. While there was no yield loss to CO and $CO_2$ at any of the stirring rates studied, the product composition varied considerably, as set forth in the following table:

| Product Components | Mole % in Product as a Function of Stirring Rate | | |
|---|---|---|---|
| | 600 RPM | 1400 RPM | 2000 RPM |
| β-TRI | 52 | 14 | 9 |
| DCE | 20 | 36 | 36 |
| TETRA | 2 | 4 | 4 |
| TRI | 6 | 27 | 31 |
| PENTA | 0 | 0 | 0 |
| PER | 16 | 16 | 16 |
| HEXA | 0 | 0 | 0 |

Absent in the product were ethylene dichloride, methyl chloroform and unsymmetrical tetrachloroethane. This example shows the beneficial effect of gas dispersion on the trichloroethylene:perchloroethylene ratio in the product.

EXAMPLE 9

β-Trichloroethane was passed at the rate of 2 cc./minute through a melt (350° C.) consisting of 4 moles CuCl, 1 mole $CuCl_2$, 1 mole $FeCl_3$, 5 moles KCl. The oxidation level of the melt was 33%. The product was recycled (passed) through the melt; the results are reported in the following table:

| Product Components | Mole % in Product as a Function of Recycling | | | |
|---|---|---|---|---|
| | First Feed | First Pass | Second Pass | Third Pass |
| βTRI | 100 | 56 | 28 | 15 |
| DCE | | 20 | 28 | 33 |
| TETRA; | | 7 | 14 | 14 |
| TRI | | 12 | 22 | 28 |
| PENTA | | 0 | 0 | 0 |
| PER | | 4 | 7 | 9 |
| HEXA | | 0 | 0 | 0 |
| TRI/PER Ratio | | 3 | 3 | 3 |

It is apparent that by proper control of contact time and gas dispersion the product yield and selectivity can be controlled.

What is claimed is:

1. A process which comprises chlorinating a material of the group consisting of $C_2$ hydrocarbons, incompletely chlorinated derivates of $C_2$ hydrocarbons, and mixtures thereof, containing at least 50% by weight of at least one of 1,1,2-trichloroethane and dichloroethylene to produce a chlorinated product containing one or more of trichloroethylene and perchloroethylene, at a temperature within the range of 300°–500° C., by means of a melt consisting essentially of iron chloride, copper chloride and alkali metal chloride by dispersing the material to be chlorinated in the melt whereby said material is chlorinated by the melt; withdrawing a gaseous effluent from the reaction zone which contains unreacted starting material and the resulting chlorinated hydrocarbon products and recovering the chlorinated hydrocarbon products from the effluent as the product of the process wherein:

(a) the alkali metal chloride is selected from the group consisting of sodium chloride, potassium chloride, rubidium chloride, cesium chloride, and mixtures thereof;

(b) the mole ratio of iron chloride to copper chloride is from about 0.1:1 to about 2:1, (c) the mole ratio of alkali metal chloride to combined moles of iron and copper chlorides is from about 0.5:1 to about 2:1; and (d) at least some of the copper chloride is cupric chloride and substantially all of the iron chloride is ferric chloride.

2. A chlorination process in accordance with claim 1 wherein the alkali metal chloride is potassium chloride.

3. A process in accordance with claim 1 which is carried out under pressure within the range of 1 atmosphere to 10 atmospheres.

4. The process of claim 1 wherein the melt is regenerated with a combination of an oxygen-containing gas and hydrogen chloride.

5. The process of claim 1 wherein the melt is regenerated with a combination of an oxygen-containing gas and hydrogen chloride.

* * * * *